United States Patent
Doering et al.

(10) Patent No.: US 10,596,080 B2
(45) Date of Patent: *Mar. 24, 2020

(54) OIL BLEND FOR MICROEMULSIONS

(71) Applicant: Henkel AG & Co. KGaA, Duesseldorf (DE)

(72) Inventors: Thomas Doering, Dormagen (DE); Stefanie Schmitz, Moenchengladbach (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 0 days.

This patent is subject to a terminal disclaimer.

(21) Appl. No.: 16/102,498

(22) Filed: Aug. 13, 2018

(65) Prior Publication Data

US 2019/0060184 A1 Feb. 28, 2019

(30) Foreign Application Priority Data

Aug. 24, 2017 (DE) ........................ 10 2017 214 799

(51) Int. Cl.

| | | |
|---|---|---|
| *A61K 8/06* | (2006.01) | |
| *A61K 8/26* | (2006.01) | |
| *A61K 8/34* | (2006.01) | |
| *A61K 8/37* | (2006.01) | |
| *A61K 8/86* | (2006.01) | |
| *A61K 8/87* | (2006.01) | |
| *A61K 8/92* | (2006.01) | |
| *A61Q 15/00* | (2006.01) | |

(52) U.S. Cl.
CPC ............. *A61K 8/068* (2013.01); *A61K 8/062* (2013.01); *A61K 8/26* (2013.01); *A61K 8/345* (2013.01); *A61K 8/37* (2013.01); *A61K 8/86* (2013.01); *A61K 8/87* (2013.01); *A61K 8/922* (2013.01); *A61Q 15/00* (2013.01); *A61K 2800/21* (2013.01); *A61K 2800/262* (2013.01); *A61K 2800/591* (2013.01)

(58) Field of Classification Search
CPC .......... A61K 8/068; A61K 8/062; A61K 8/26; A61K 8/345; A61K 8/37; A61K 8/86; A61K 8/87; A61K 8/922; A61K 2800/262; A61K 2800/21; A61K 2800/591; A61Q 15/00
See application file for complete search history.

(56) References Cited

U.S. PATENT DOCUMENTS

| | | | |
|---|---|---|---|
| 3,887,692 A | 6/1975 | Gilman | |
| 3,904,741 A | 9/1975 | Jones et al. | |
| 4,017,599 A | 4/1977 | Rubino | |
| 4,359,456 A | 11/1982 | Gosling et al. | |
| 4,384,974 A * | 5/1983 | Guthauser | A61K 47/00 424/170 |
| 4,775,528 A | 10/1988 | Callaghan et al. | |
| 4,880,563 A * | 11/1989 | Dahms | A61K 8/06 514/772 |
| 6,010,688 A | 1/2000 | Shen | |
| 2015/0283048 A1 | 10/2015 | Banowski et al. | |
| 2017/0281517 A1* | 10/2017 | Doering | A61K 8/062 |

FOREIGN PATENT DOCUMENTS

| | | |
|---|---|---|
| GB | 1347950 A | 2/1974 |
| GB | 2048229 A | 12/1980 |
| WO | 1996028132 A2 | 9/1996 |
| WO | 2000061083 A1 | 10/2000 |
| WO | 03086339 A1 | 10/2003 |
| WO | 2006136330 A1 | 12/2006 |
| WO | 2018111704 A1 | 6/2018 |
| WO | 2018111706 A1 | 6/2018 |

* cited by examiner

*Primary Examiner* — Shirley V Gembeh
(74) *Attorney, Agent, or Firm* — Lorenz & Kopf, LLP

(57) ABSTRACT

The present disclosure relates to antiperspirant and/or deodorizing cosmetic agents in the form of oil-in-water emulsions, which contain a combination of isopropylisostearate and isopropylmyristate as cosmetic oils and a small total quantity of oils and emulsifiers. The cosmetic agent as contemplated herein surprisingly have extremely low or no stickiness after their application to the skin. They can also be optically transparent and have improved storage stability.

20 Claims, No Drawings

OIL BLEND FOR MICROEMULSIONS

CROSS-REFERENCE TO RELATED APPLICATIONS

This application claims priority to German Patent Application No. 10 2017 214 799.7, filed Aug. 24, 2017, which is incorporated herein by reference in its entirety.

TECHNICAL FIELD

The present disclosure relates to antiperspirant and/or deodorizing cosmetic agents in the form of emulsions, which contain a combination of specified proportions of selected oils and a small total quantity of oils and emulsifiers. The cosmetic agents as contemplated herein surprisingly have extremely low or no stickiness after their application to the skin. Furthermore, they are generally optically transparent and have an improved storage stability.

BACKGROUND

Washing, cleaning and care for the body are a basic human need and modern industry continuously attempts to meet these human needs in a variety of ways. Long-lasting elimination or at least reduction of the body odor and underarm wetness are especially important for daily hygiene.

Body odor is caused by the bacterial decomposition of the constituents of the initially odorless sweat. The decomposition products, which contribute significantly to the body odor, in particular to the axillary body odor, can be divided into three classes: short-chain $C_4$-$C_{10}$ fatty acids, which may be linear, branched, saturated and unsaturated (for example, isovaleric acid, 3M2H) constitute the first class, short-chain linear or branched sulfanyl alcohols constitute the second class, the third class includes various steroid hormones and their metabolic products (for example, 5-alpha androstenol and 5-α androstenone).

Body odor can therefore be combated by preventing the bacterial decomposition of the sweat. State-of-the-art antimicrobial substances are used to prevent the bacterial decomposition of the sweat. These reduce the number of sweat-decomposing bacteria on the skin by killing them and/or inhibiting the growth of these bacteria. Active substances are also known that reduce and/or prevent the formation of decomposition products by blocking bacterial enzymes. It is furthermore a commonly known fact that volatile decomposition products are absorbed by physical and/or chemical interaction, which avoids unpleasant body odor.

Moreover, body odor can be combated by preventing the perspiration of the body. Cosmetic antiperspirants from the prior art contain at about least one antiperspirant salt. To achieve a high degree of sweat reduction, aluminum zirconium halides are preferably used in the prior art. The antiperspirant effect of these salts can be further improved by thermal treatment and the addition of ligands or phosphates, for example.

Such agents of the prior art can generally lead to an impaired skin tolerance due to the high emulsifier content required to stabilize the emulsion. Furthermore, when such agents of the prior art are applied textile stains can form, which are perceived as undesirable by the consumer. Cosmetic agents in the form of microemulsions that have a comparatively lower emulsifier content have therefore also already been developed. For example, WO96/28132 A2 discloses microemulsion gels as the basis for deodorizing or antiperspirant preparations, containing at least one polyethoxylated and/or polypropoxylated O/W emulsifier.

Antiperspirant agent in the form of oil-in-water emulsions are also disclosed in WO00/61083 A1, which deals with the problem of the stickiness of cosmetic antiperspirant agents. A combination of nonionic emulsifiers and oil components is disclosed, wherein the total quantity of emulsifiers and oil components is low. The stickiness of the skin feeling could however be improved further.

Moreover, the transparent appearance of cosmetic agents is frequently desired by consumers. Cosmetic agents in the form of transparent emulsions are known. For transparent emulsions, the droplets distributed in the dispersed phase should have as small a mean particle diameter as possible, generally significantly below about 1000 nm, preferably below about 400 nm or even below about 200 nm.

The present disclosure therefore addressed the problem of preparing antiperspirant cosmetic agents in the form of microemulsions that are as transparent as possible, which typically have no or a very low sticky sensation after application to the skin and a high storage stability, good skin tolerance, as well as low residue formation, especially on textiles.

Surprisingly, this problem was addressed by the fact that the cosmetic agents contain a combination of very specific cosmetic oils in specified proportions and at least one nonionic emulsifier. Due to a low total quantity of emulsifiers, good skin tolerance can also be achieved.

BRIEF SUMMARY

Cosmetic agents are provided herein. In an embodiment, a cosmetic agent is provided in the form of an O/W emulsion. The cosmetic agent includes, in an aqueous cosmetically compatible carrier, a) isopropylisostearate, b) isopropylmyristate, c) a non-ionic emulsifier, and d) at least one antiperspirant and/or deodorizing active ingredient. The isopropylisostearate a) is present in a quantity of from about 0.5 to about 3.0 wt. %, based on the total weight of the cosmetic agent. The isopropylmyristate b) is present in a quantity of from about 0.1 to about 1.0 wt. %, based on the total weight of the cosmetic agent. The non-ionic emulsifier c) is selected from c1) at least one ethoxylated, saturated, branched $C_{14}$-$C_{18}$ alcohol with an ethoxylation degree of from about 18 to about 22 ethylene oxide units, c2) at least one ethoxylated, linear, mono-unsaturated $C_{16}$-$C_{20}$ alcohol with an ethoxylation degree of from about 18 to about 22 of ethylene oxide units and c3) combinations thereof. The weight ratio of the isopropylisostearate to the isopropylmyristate is from about 1.5:1 to about 3.5:1. The total quantity of emulsifiers and oil components a) and b) in the cosmetic agent is from about 1.5 to about 8.0 wt. %, relative to the total weight of the cosmetic agent.

In another embodiment, a cosmetic agent is provided in the form of an O/W emulsion. The cosmetic agent includes, in an aqueous cosmetically compatible carrier, a) isopropylisostearate, b) isopropylmyristate, c) a non-ionic emulsifier, d) at least one antiperspirant and/or deodorizing active ingredient, at least one further non-ionic emulsifier, and at least one polyethylene glycol ether and/or at least one non-ionic polyurethane polymer. The isopropylisostearate a) is present in a quantity of from about 0.5 to about 3.0 wt. %, based on the total weight of the cosmetic agent. The isopropylmyristate b) is present in a quantity of from about 0.1 to about 1.0 wt. %, based on the total weight of the cosmetic agent. The composition includes from about 0.1 wt. % or less of ionic surfactants. The non-ionic emulsifier c) is selected from c1) at least one ethoxylated, saturated, branched $C_{14}$-$C_{18}$ alcohol with an ethoxylation degree of from about 18 to about 22 ethylene oxide units, c2) at least one ethoxylated, linear, mono-unsaturated $C_{16}$-$C_{20}$ alcohol with an ethoxylation degree of from about 18 to about 22 of ethylene oxide units and c3) combinations thereof. The weight ratio of the isopropylisostearate to the isopropylmyristate is from about 1.5:1 to about 3.5:1. The total quantity of emulsifiers and oil components a) and b) in the cosmetic agent is from about 1.5 to about 8.0 wt. %, relative to the total weight of the cosmetic agent. The at least one further non-ionic emulsifier is selected from hydrogenated castor oils with from about 20 mol to about 60 of ethylene oxide per mol of hydrogenated castor oil, esters of isostearic acid with 1,2-propylene glycol, and combinations thereof. The at least one polyethylene glycol ether is of the general formula R—O—(—$CH_2$—$CH_2$—O—)$_n$—R', wherein R and R' independently denote branched or unbranched alkyl, aryl or alkenyl radicals and n is an integer greater than about 75. The at least one non-ionic polyurethane polymer comprises at least one polyurethane unit of the formula (Ib) and/or the formula (Ic), at least one nonionic polyether unit of the formula (IIa) and at least one ether unit of the formula (IIIb),

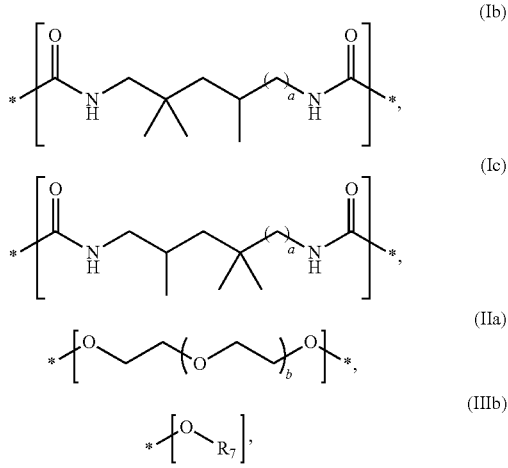

wherein
a denotes the integer 2,
b denotes integers from about 80 to 110, and
$R_7$ denotes a branched $C_{16}$-$C_{20}$ alkyl group.

DETAILED DESCRIPTION

The following detailed description is merely exemplary in nature and is not intended to limit the disclosure or the application and uses of the subject matter as described herein. Furthermore, there is no intention to be bound by any theory presented in the preceding background or the following detailed description.

In particular, the present disclosure relates to the following points:

Cosmetic agent in the form of an O/W emulsion, containing in an aqueous cosmetically compatible carrier:
a) Isopropylisostearate in a quantity of from about 0.5 to about 3.0 wt. %, based on the total weight of the cosmetic agent,
b) Isopropylmyristate in a quantity of from about 0.1 to about 1.0 wt. %, based on the total weight of the cosmetic agent, wherein the weight ratio of the isopropylisostearate to the isopropylmyristate is from about 1.5:1 to about 3.5:1
c) a non-ionic emulsifier, selected from c1) at least one ethoxylated, saturated, branched $C_{14}$-$C_{18}$ alcohol with an ethoxylation degree of from about 18 to about 22 ethylene oxide units, c2) at least one ethoxylated, linear, mono-unsaturated $C_{16}$-$C_{20}$ alcohol with an ethoxylation degree of from about 18 to about 22 of ethylene oxide units and c3) combinations thereof, and
d) at least one antiperspirant and/or deodorizing active ingredient, wherein the total quantity of emulsifiers and oil components a) and b) in the cosmetic agent is from about 1.5 to about 8.0 wt. %, relative to the total weight of the cosmetic agent.

Cosmetic agent according to point 1, exemplified in that the total quantity of emulsifiers and oil components a) and b) in the cosmetic agent is from about 2.5 to about 6.0 wt. %, relative to the total weight of the cosmetic agent.

Cosmetic agent according to points 1 and 2, exemplified in that the isopropylisostearate is contained in a quantity of from about 0.7 to about 1.5 wt. % and the isopropylmyristate in a quantity of from about 0.3 to about 0.7 wt. %, relative to the total weight of the cosmetic agent.

Cosmetic agent according to one of the points above, exemplified in that the weight ratio of isopropylisostearate to isopropylmyristate is from about 1.5:1 to about 3.5:1, preferably from about 1.8:1 to about 2.5:1.

Cosmetic agent according to one of the points above, exemplified in that the non-ionic emulsifier c) is a combination c3) of non-ionic emulsifiers c1) and c2), wherein the weight ratio of non-ionic emulsifier c1) to non-ionic emulsifier c2) is from about 1.2:1 to about 3.5:1, preferably from about 1.5:1 to about 2.5:1.

Cosmetic agent according to the claim in one of the points above, exemplified in that nonionic emulsifier c1) is polyoxyethylene (20) isocetyl ether (INCI: isoceteth-20) and nonionic emulsifier c2) is polyoxyethylene (20) oleyl ether (INCI: oleth-20).

Cosmetic agent according to one of the points above, exemplified in that the total quantity of non-ionic emulsifier c1) is from about 1.0 to about 5.0 wt. % and the total quantity of non-ionic emulsifier c2) is from about 0.5 to about 3.0 wt. %, relative to the total weight of the cosmetic agent.

Cosmetic agent according to one of the points above, exemplified in that it contains at least one further non-ionic emulsifier, which is selected from hydrated castor oils with from about 20 mol to about 60 of ethylene oxide per mol of hydrated castor oil, preferably hydrogenated castor oil with around about 40 mol of ethylene oxide per mol of hydrogenated castor oil (INCI: PEG-40 Hydrogenated Castor Oil), esters of isostearic acid with 1,2-propylene glycol, preferably propylenglycolmonoisostearate, and combinations thereof.

Cosmetic agent according to one of the points above, exemplified in that it contains from about 0.1 wt. % or less of ionic surfactants.

Cosmetic agent according to one of the points above, exemplified in that it contains at least one antiperspirant active ingredient in a total quantity of from about 2.0 to about 40 wt. %, preferably from about 5.0 to about 30 wt. %, more preferably from about 8.0 to about 25 wt. %, and most preferably from about 10 to about 20 wt. %, relative to the total weight of the cosmetic agent.

Cosmetic agent according to one of the points above, exemplified in that it contains at least one polyethylene glycol ether of the general formula R—O—(—CH$_2$—CH$_2$—O—)$_n$—R', wherein R and R' independently denote branched or unbranched alkyl, aryl or alkenyl radicals and n is an integer greater than about 75, preferably an integer from about 100 to about 400, and particularly preferably an integer from about 120 to about 200, preferably PEG-150 Distearate and/or PEG-150 Dioleate; and/or at least one non-ionic polyurethane polymer, which comprises at least one polyurethane unit of the formula (Ib) and/or the formula (Ic), at least one nonionic polyether unit of the formula (IIa) and at least one ether unit of the formula (IIIb),

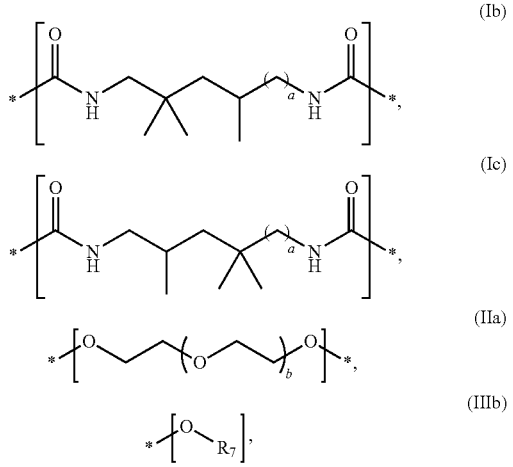

wherein
a denotes the integer 2,
b denotes integers from about 80 to about 110, and
R$_7$ denotes a branched C$_{16}$-C$_{20}$ alkyl group.

Cosmetic agent according to one of the points above, exemplified in that it contains the at least one deodorizing active ingredient in a total quantity of from about 0.0001 to about 40 wt. %, preferably from about 0.2 to about 20 wt. %, more preferably from about 1.0 to about 15 wt. %, and most preferably from about 1.5 to about 5.0 wt. %, relative to the total weight of the cosmetic agent.

Cosmetic agent according to one of the points above, exemplified in that the agent is provided in the form of an O/W emulsion with a volume average droplet size of from about 50 to about 1000 nm, preferably from about 100 to about 500 nm, more preferably from about 150 to about 400 nm, and most preferably from about 200 to about 300 nm.

Cosmetic agent according to one of the points above, exemplified in that the agent has a viscosity of from about 1200 to about 2500 cps (20° C., Brookfield, Spindle 3, 20 rpm).

Cosmetic agent according to one of the points above, exemplified in that the agent has a measured turbidity according to DIN EN ISO 7027 (C2) 2016-11 at 22° C. of from 0 to about 150 NTU, preferably to about 80 NTU, more preferably to about 60 NTU, and particularly preferably to about 40 NTU.

Non-therapeutic cosmetic method for reducing the perspiration of the body and/or for reducing the body odor released by perspiration, wherein the cosmetic agent according to one of points 1 to 15 is applied to the human skin and remains on the application point for at least about 1 hour.

As contemplated herein, the term "emulsifiers" should be understood as compounds that can reduce the interface tension between the different phases of the cosmetic agents and, in this manner, lead to a stabilization of the cosmetic agents. Such emulsifiers have an amphiphilic molecular structure, i.e. they have both polar and apolar groups. The polar groups are groups that have a hydrophilic character. Apolar groups are understood as hydrophobic and lipophilic groups. These emulsifiers can therefore interact with both hydrophilic and lipophilic phases. Consequently, an orientation of the emulsifiers occurs at the boundary surface between the hydrophilic and hydrophobic phase, whereby stabilization is achieved. Surfactants and "emulsifiers" form adsorption layers on the top and boundary surfaces or can aggregate in volume phases to form micelle colloids or lyotropic mesophases. Besides the oriented absorption at boundary surfaces, basic properties of the surfactants and emulsifiers are the aggregation to micelles and the formation of lyotropic phases.

The term "HLB value" also used in this description is understood as a measure introduced by Griffin in 1950 for the water or oil solubility of predominantly non-ionic surfactants. The HLB value can be determined experimentally by using, for example, the phenol titration method, in which the emulsifier solution is mixed with a 5% phenol solution until it becomes cloudy. Furthermore, the HLB value can also be determined (gas) chromatographically by determining the permittivity or colorimetrically. The HLB value of an emulsifier mixture can be additively calculated using the values of its constituents. The scale of HLB values generally ranges from about 1 to about 20. Substances with a low HLB value of below about 8 are generally good water-in-oil emulsifiers, while hydrophilic compounds with an HLB value of about 8 and above act as oil-in-water-emulsifiers.

As contemplated herein, the term "antiperspirant active ingredient" should be understood as active ingredient that lead to a prevention or reduction of the perspiration of the sweat glands of the body.

Furthermore, as contemplated herein, the term "deodorizing active ingredient" should be understood as active ingredients that lead to a reduction or prevention of the bacterial decomposition of the sweat and/or absorb or cover the malodorous volatile decomposition products.

Finally, the total quantity of emulsifiers is understood as the total amount of all emulsifiers contained in the cosmetic agent.

Unless otherwise specified, the wt. % presently relates to the total weight of the cosmetic agents, wherein the sum of all ingredients of the agents amounts to 100 wt. %.

The cosmetic agents as contemplated herein contain oil components a), oil components b), non-ionic emulsifier c) and at least one antiperspirant or deodorizing active ingredient d), as well as, where appropriate, additional ingredients in a cosmetically compatible carrier.

Preferred cosmetically compatible carriers are aqueous, alcoholic or aqueous-alcoholic media preferably having at least about 10 wt. % water, relative to the total weight of the cosmetic agent. It is particularly preferable that the cosmetically acceptable carrier contains water, particularly in a quantity that is preferably at least about 10 wt. %, more preferably at least about 20 wt %., most preferably at least about 40 wt. % water relative to the total weight of the cosmetic agent. Particularly preferred cosmetic agents have a proportion of water of from about 50 to about 95 wt. %, preferably from about 60 to about 90 wt. % and particularly from about 65 to about 85 wt. %, relative to their total weight.

Low alcohols having from about 1 to about 4 carbon atoms are normally used for cosmetic purpose, such as ethanol and isopropanol, can be used, in particular as alcohols. Examples of water-soluble solvents as a cosolvent are glycerol and/or ethylene glycol and/or 1,2-propylene glycol, which can each be used in a quantity of from about 0 to about 5.0 wt. % relative to the total weight of the cosmetic agent.

The cosmetic agent as contemplated herein contains as necessary oil components a) isopropylisostearate in a quantity of from about 0.5 to about 3.0 wt. %, relative to the total weight of the cosmetic agent, and b) isopropylmyristate in a quantity of from about 0.1 to about 1.0 wt. %, relative to the total weight of the cosmetic agent. Surprisingly, it has been found that with this special combination of oil components, emulsions were obtained that were not sticky to the touch after application to the skin, when these oil components were used together with specific emulsifier(s) c) and the total quantity of oil components a) and b) and emulsifiers is from about 1.5 to about 8.0 wt. %.

Furthermore, it is preferred as contemplated herein if the isopropylisostearate a) is contained in a quantity of from about 0.7 to about 1.5 wt. %, more preferably from about 1.0 to about 1.5 wt. %, relative to the total weight of the cosmetic agent. It is preferred as contemplated herein if the isopropylmyristate b) is contained in the cosmetic agent in a quantity of from about 0.3 to about 0.7 wt. %, more preferably from about 0.4 to about 0.6 wt. %, relative to the total weight of the cosmetic agent.

It is additionally preferred as contemplated herein if the weight ratio of isopropylisostearate to isopropylmyristate in the cosmetic agent is from about 1.5:1 to about 3.5:1, preferably from about 1.8:1 to about 2.5:1.

In preferred embodiments of the present disclosure, it contains no further cosmetic oils other than the isopropylisostearate and isopropylmyristate. Other preferred embodiments of the present disclosure can contain further oil components, preferably in a total quantity of less than about 5 wt. %, more preferably about 3 wt. %, or less than about 2 wt. % relative to the weight of the cosmetic agent.

Further oil components that can be contained are preferably selected from (i) volatile non-silicone oils, in particular liquid paraffin oils and isoparaffin oils, such as isodecane, isoundecane, isododecane, isotridecane, isotetradecane, isopentadecane, isohexadecane and isoeicosane; (ii) non-volatile non-silicone oils, in particular the esters of linear or branched, saturated or unsaturated $C_{2-30}$-fatty alcohols with linear or branched, saturated or unsaturated $C_{2-30}$-fatty acids, which can be hydroxylated, the $C_8$-$C_{22}$-fatty alcohol esters of monohydric or polyhydric $C_2$-$C_7$-hydroxycarboxylic acids, the triethyl citrates, the branched saturated or unsaturated $C_{6-30}$-fatty alcohols, the mono-, di- and triglycerides of linear or branched, saturated or unsaturated, optionally hydroxylated $C_{8-30}$-fatty acids, the dicarboxylic acid esters of linear or branched $C_2$-$C_{10}$-alkanols, the addition products of ethylene oxide and/or propylene oxide onto mono- or multivalent $C_{3,22}$-alkanols, which may optionally be esterified, the symmetrical, asymmetric or cyclic esters of carbonic acid with fatty alcohols, the esters of dimeric unsaturated $C_{12-22}$-fatty acids with monohydric, linear, branched and cyclic $C_{2-18}$-alkanols or $C_{2-6}$-alkanols, the benzoic esters of linear or branched $C_{8-22}$-alkanols, such as the benzoic acid $C_{12-15}$-alkyl ester and the benzoic acid isostearyl ester and the benzoic acid octyldodecyl ester, the synthetic hydrocarbons, such as polyisobutene and polydecenes, the alicyclic hydrocarbons; and (iii) mixtures thereof.

As contemplated herein, it can also contain volatile non-silicone oils in the form of $C_{10-13}$ isoparaffin mixtures having a vapor pressure of from about 10 to about 400 Pa (from about 0.08 to about 3 mm Hg), preferably from about 13 to about 100 Pa (from about 0.1 to about 0.8 mm Hg), at about 20° C. and an environmental pressure of about 1.013 hPa.

Preferably, the total quantity of emulsifiers and oil components a) and b) in the cosmetic agent is from about 2.5 to about 6.0 wt. %, relative to the total weight of the cosmetic agent. As preferred embodiments of the present disclosure do not contain any further oil components, the total amount of emulsifiers and of all oil components in the cosmetic agent is preferably from about 1.5 to about 8.0 wt. %, more preferably from about 2.5 to about 6.0 wt. %, relative to the total weight of the cosmetic agent.

Emulsifier c) as contemplated herein contains a non-ionic emulsifier, selected from c1), an ethoxylated, saturated, branched $C_{14}$-$C_{18}$ alcohol with an ethoxylation degree of from about 18 to about 22 ethylene oxide units, c2) at least one ethoxylated, linear, mono-unsaturated $C_{16}$-$C_{20}$ alcohol with an ethoxylation degree of from about 18 to about 22 of ethylene oxide units and c3) combinations thereof.

Emulsifier c1) is preferably an ethoxylated, saturated, branched $C_{14}$-$C_{18}$ alcohol with an ethoxylation degree of about 20 ethylene oxide units, or mixtures of two or more of them. Furthermore, emulsifier c1) preferably has an HLB value of from about 10 to about 17, particularly preferably from about 14 to about 16. As contemplated herein, emulsifier c1) is particularly preferably an ethoxylated, saturated, branched $C_{16}$ alcohol with an ethoxylation degree of about 20 mol of ethylene oxide per mol of alcohol, or a mixture of these.

The compounds known under the INCI designations isosteareth-20 (HLB value=15; CAS No.: 52292-17-8) and isoceteth-20 (HLB value=15.7; CAS No.: 69364-63-2 and 9004-95-9) are preferred examples of ethoxylated branched $C_{14}$-$C_{18}$ alcohols with from about 18 to about 22 mol of ethylene oxide per mol of alcohol that can be used as contemplated herein. Of these, isoceteth-20 is particularly preferable as contemplated herein.

The cosmetic agent as contemplated herein contains at least one ethoxylated, saturated, branched $C_{14}$-$C_{18}$ alcohol with an ethoxylation degree of from about 18 to about 22 (emulsifier c1)), preferably in a total quantity of from about 1.0 to about 5.0 wt. %, more preferably from about 1.5 to about 4.0 wt. %, and particularly preferably from about 2.0 to about 3.0 wt. %.

Emulsifier c2) is at least one ethoxylated, linear, mono-unsaturated $C_{16}$-$C_{20}$ alcohol with an ethoxylation degree of from about 18 to about 22 ethylene oxide units, more preferably, the emulsifier c2) has an HLB value of from about 10 to about 17, particularly preferably from about 14 to about 16.

As contemplated herein, emulsifier c2) is preferably an ethoxylated, linear, mono-unsaturated $C_{16}$ alcohol with an ethoxylation degree of about 20 mol of ethylene oxide per mol of alcohol. A particularly preferred nonionic emulsifier c2) is oleth-20 (HLB value=15.3; CAS No.: 9004-98-2).

The cosmetic agent as contemplated herein contains the at least one emulsifier c2), wherein an ethoxylated, linear, mono-unsaturated $C_{16}$-$C_{20}$ alcohol has an ethoxylation degree of from about 18 to about 22 ethylene oxide units, preferably in a total quantity of from about 0.5 to about 3.5 wt. %, more preferably from about 0.7 to about 3.0 wt. %, and particularly preferably from about 0.8 to about 1.5 wt. %.

It is particularly preferable as contemplated herein if non-ionic emulsifier c) is a combination of non-ionic emulsifiers c1) and c2), wherein the weight ratio of non-ionic emulsifier c1) to non-ionic emulsifier c2) is from about 1.2:1 to about 3.5:1, preferably from about 1.5:1 to about 2.5:1. It is particularly preferable if non-ionic emulsifier c1) is polyoxyethylene (20) isocetyl ether (INCI: isoceteth-20) and nonionic emulsifier c2) is polyoxyethylene (20) oleyl ether (INCI: oleth-20).

In particular, it is preferred that the total quantity of non-ionic emulsifier c1) is from about 1.0 to about 5.0 wt. % and the total quantity of non-ionic emulsifier c2) is from about 0.5 to about 3.0 wt. %, relative to the total weight of the cosmetic agent. It is particularly preferred if the total quantity of non-ionic emulsifier c1) is from about 2.0 to about 3.0 wt. % and the total quantity of non-ionic emulsifier c2) is from about 0.8 to about 1.5 wt. %, relative to the total weight of the cosmetic agent.

In addition to the specified non-ionic emulsifiers, other emulsifiers can be contained in the cosmetic agent as contemplated herein. This can include other nonionic emulsifiers and, in small quantities, also ionic surfactants, i.e. cationic, anionic and/or zwitterionic or amphoteric surfactants. Ionic surfactants are preferably contained in the present disclosure, but only in a total quantity of about 0.2 wt. % or less, more preferably about 0.1 wt. % or less. Cationic surfactants up to about 0.1 wt. % can be contained in embodiments of the present disclosure. Anionic surfactants are particularly preferably not contained in the cosmetic agent as contemplated herein, i.e. preferably in a total quantity of 0 wt. %.

Further nonionic emulsifiers that may be contained are preferably those with an HLB value of from about 10 to about 17 that do not fall under the definitions of emulsifier c1) and emulsifier c2). These are selected, for example, from the group of mono- and/or di- and/or triglycerides of coconut oil with about 7 mol of ethylene oxide per mol of glyceride, mono- and/or diglycerides of almond oil with from about 20 to about 60 mol of ethylene oxide per mol of glyceride, hydrogenated castor oil with from about 25 mol to about 60 mol of ethylene oxide per mol of hydrogenated castor oil, N-(2-hydroxyethyl)octadecanamide, mono- and/or tri-sorbitan oleates with about 20 mol of ethylene oxide per mol of sorbitan, mono-sorbitan stearates and/or mono-sorbitan laurates with about 20 mol of ethylene oxide per mol of sorbitan, ethoxylated fatty acids from olive oil with about 7 mol of ethylene oxide per mol of fatty acid, $C_{16}$-$C_{18}$ alkyl glucosides, esters of oleic acid and/or lauric acid with about 8 mol of ethylene oxide per mol of acid, polymers of methyl-D-glucopyranoside dioctadecanoate with glycerol, N-(2-hydroxyethyl)dodecanamide, methyl-β-D-glucoside sesquistearates with about 20 mol of ethylene oxide per mol of glucose ester. The mono- and/or di- and/or triglycerides of coconut oil with about 7 mol of ethylene oxide per mol of glyceride used in the context of the present disclosure is, for example, the compound known under the INCI designation PEG-7 Glyceryl Cocoate (HLB value=10; CAS No.: 68201-46-7). Additional emulsifiers used in the context of the present disclosure in the form of mono- and/or diglycerides of almond oil with from about 20 to about 60 mol of ethylene oxide per mol of glyceride, preferably with an HLB value of from about 10 to about 17, are, for example, the compounds known under the INCI designations PEG-20 Almond Glycerides (HLB value=10; CAS No.: 124046-50-0) and PEG-60 Almond Glycerides (HLB value=15; CAS No.: 226993-90-4). Other suitable additional emulsifiers are hydrogenated castor oil with 25 mol of ethylene oxide per mol of hydrogenated castor oil, which is known under the INCI designation PEG-25 Hydrogenated Castor Oil (HLB value=10.8; CAS No.: 61788-85-0), or preferably hydrated castor oil with 40 mol of ethylene oxide per mol of hydrogenated castor oil with the INCI designation PEG-40 Hydrogenated Castor Oil (HLB value=14-16). Additional mono- and/or tri-sorbitan oleates with 20 mol of ethylene oxide per mol of sorbitan used as contemplated herein include, for example, the compounds known under the INCI designations polysorbate 80 (HLB value=15; CAS No.: 9005-65-6) and polysorbate 85 (HLB value=11; CAS No.: 9005-70-3). Furthermore, mono-sorbitan stearates and/or mono-sorbitan laurates with 20 mol of ethylene oxide per mol of sorbitan, preferably with an HLB value of from about 10 to about 17, which, for example, are known under the INCI designations polysorbate 60 (HLB value=14.9; CAS No.: 9005-67-8) and polysorbate 20 (HLB value=16.7; CAS No.: 9005-64-5), are also suitable as additional emulsifiers. The compounds known under the INCI designations oleth-10 (HLB value=12.4; CAS No.: 9004-98-2), ceteth-10 (HLB value=12.9; CAS No.: 9004-95-9), ceteareth-20 (HLB value=15.2; CAS No.: 68439-49-6), steareth-20 (HLB value=15.3; CAS No.: 9005-00-9), steareth-21 (HLB value=15.5; CAS No.: 9005-00-9), ceteth-20 (HLB value=15.7; CAS No.: 9004-95-9) and Laureth-23 (HLB value=16.9; CAS No. 9002-92-0) are examples of additional ethoxylated linear $C_{10}$-$C_{22}$ alcohols with from about 10 to about 23 mol of ethylene oxide per mol of alcohol used as contemplated herein, which are not included among the emulsifiers a) and b). Ethoxylated fatty acids from olive oil with 7 mol of ethylene oxide per mol of fatty acid and $C_{16}$-$C_{18}$ alkyl glucoside, preferably with an HLB value of from about 10 to about 17, which, for example, are known under the INCI designations PEG-7 Olivate (HLB value=11; CAS No.: 226708-41-4) and cetearyl glucoside (HLB value=11; CAS No.: 54549-27-8 (C16), 27836-65-3 (C18)), are also suitable as additional emulsifiers. Furthermore, esters of oleic acid and/or lauric acid with 8 mol of ethylene oxide per mol of acid and polymers of methyl-D-glucopyranoside dioctadecanoate with glycerol may be used, which, for example, are known under the INCI designations PEG-8 Oleate (HLB value=11.6; CAS No.: 9004-96-0), PEG-8 Laurate (HLB value=13; CAS No.: 9004-81-3) and polyglyceryl-3 methylglucose distearate (HLB value=12; CAS No.: 68986-95-8), can be used as contemplated herein Finally, methyl β-D-glucoside sesquistearates with about 20 mol of ethylene oxide per mol of glucose ester, which, for example, are known under the INCI designation PEG-20 Methyl Glucose Sesquistearate (HLB value=15; CAS No.: 68389-70-8), are also used as contemplated herein. The total weight of these optional additionally contained emulsifiers is preferably zero to about 2 wt. %, more preferably from about 0.1 to about 1.5 wt. %, particularly preferably from about 0.5 to about 1 wt. %, relative to the total weight of the cosmetic agents as contemplated herein.

At least one nonionic emulsifier with an HLB value of from about 1 to about 6 can also be contained in preferred embodiments of the present disclosure. Preferred cosmetic agents as contemplated herein are exemplified in that the at least one emulsifier with an HLB value of from about 1 to about 6 is selected from the group of mono- and/or diesters of sorbitan with oleic acid, stearic acid or isostearic acid, esters of isostearic acid with propylene oxide, lecithins, ethoxylated $C_{12}$-$C_{20}$ alcohols with 2 mol of alcohol per mol of ethylene oxide, and in particular esters of isostearic acid with 1,2-propylene glycol.

A particularly preferable ester of isostearic acid with 1,2-propylene glycol used as contemplated herein is, for example, the compound known under the INCI designation propylene glycol isostearate (HLB value=2.5; CAS No.: 63799-53-1).

The at least one emulsifier with an HLB value of from about 1 to about 6, preferably the esters of isostearic acid with 1,2-propylene glycol, in particular 2-hydroxypropyl-16-methyl heptadecanoate (INCI: propylene glycol monoisostearate), is preferably contained in specific quantity ranges.

Preferred cosmetic agent as contemplated herein are therefore exemplified in that the at least one emulsifier with an HLB value from about 1 to about 6 is contained in a total amount of from about 0.1 to about 1.7 wt. %, preferably from about 0.2 to about 1.5 wt. %, more preferably from about 0.3 to about 1.2 wt. %, particularly preferably from about 0.4 to about 1.0 wt. %, relative to the total weight of the cosmetic agent.

The aforementioned quantities relate to the total quantity of emulsifiers with an HLB value of from about 1 to about 6. Consequently, if about 2 or more emulsifiers with an HLB value of from about 1 to about 6 are used, the aforementioned quantities relate to their total quantity.

In the cosmetic agents as contemplated herein, the weight ratio of the sum of the emulsifiers a) and b) to the emulsifier with an HLB value of from about 1 to about 6 is preferably from about 10:1 to about 2:1, more preferably from about 8:1 to about 3:1. The use of the weight ratios listed above can contribute to an improvement in stability under temperature fluctuations.

As contemplated herein, the total quantity of emulsifiers in the cosmetic agent is from about 1.5 to about 8.0 wt. %, more preferably from about 2.0 to about 7.0 wt. %, and particularly preferably from about 3.0 to about 6.0 wt. %. Due the low emulsifier concentration, the cosmetic agents as contemplated herein have a high skin tolerance and excellent cosmetic properties.

As a further essential constituent d), the cosmetic agent as contemplated herein contains at least one antiperspirant and/or deodorizing active ingredient.

Aluminum salts and/or aluminum zirconium salts are preferably used as antiperspirant active ingredients in the context of the present disclosure. Cosmetic agents as contemplated herein are therefore exemplified in that the at least one antiperspirant active ingredient is selected from the group of (i) water-soluble astringent inorganic salts of aluminum, in particular aluminum chlorohydrate, aluminum sesquichlorohydrate, aluminum dichlorohydrate, aluminum hydroxide, potassium aluminum sulphate, aluminum bromohydrate, aluminum chloride, aluminum sulphate; (ii) water-soluble astringent organic salts of aluminum, in particular aluminum chlorohydrex-propylene glycol, aluminum chlorohydrex-poly ethylene glycol, aluminum-propylene glycol complexes, aluminum s es qui chl orohy drex-propylene glycol, aluminum s es quichl orohy drex-poly ethylene glycol, aluminum-propylene gly col-di chl orohy drex, aluminum-polyethylene gly col-di chl orohy drex, sodium aluminum lactate, sodium aluminum hydroxy lactate, aluminum lipo amino acids, aluminum lactate, aluminum chlorohydroxyallantoinate, sodium aluminum chlorohydroxy lactate; (iii) water-soluble astringent inorganic aluminum zirconium salts, in particular aluminum zirconium trichlorohydrate, aluminum zirconium tetrachlorohydrate, aluminum zirconium pentachlorohydrate, aluminum zirconium octachlorohydrate; (iv) water-soluble astringent organic aluminum zirconium salts, in particular aluminum zirconium propylene glycol complexes, aluminum zirconium trichlorohydrex glycine, aluminum zirconium tetrachlorohydrex glycine, aluminum zirconium pentachlorohydrex glycine, aluminum zirconium octachlorohydrex glycine; and (v) mixtures thereof.

As contemplated herein, the expression "antiperspirant aluminum salts" does not include alumosilicates or zeolithes. Moreover, as contemplated herein, water-soluble aluminum salts are those salts which have a solubility of at least about 3 wt. % at 20° C., i.e. at least about 3 g of the antiperspirant aluminum salt dissolve in about 97 g of water at 20° C.

Particularly preferred inorganic aluminum salts are selected from aluminum chlorohydrate, particularly aluminum chlorohydrate with the general formula $[Al_2(OH)_5Cl.1-6\ H_2O]_n$, preferably $[Al_2(OH)_5Cl.2-3\ H_2O]_n$, which can be in non-activated (polymerized) or in activated form (depolymerized), as well as aluminum chlorohydrate with the general formula $[Al_2(OH)_4Cl_2.1-6\ H_2O]_n$, preferably $[Al_2(OH)_4Cl_2.2-3\ H_2O]_n$, which can be in non-activated (polymerized) or in activated form (depolymerized). The production of such antiperspirant aluminum salts is disclosed, for example, in the publications U.S. Pat. Nos. 3,887,692 A, 3,904,741 A, 4,359,456 A, GB 2 048 229 A and GB 1 347 950 A.

As contemplated herein, particularly preferred antiperspirant aluminum salts are selected from so-called "activated" aluminum salts, which are also designated as antiperspirant active ingredients "with enhanced activity". Such active ingredients are known from the prior art and are also commercially available. Their production is disclosed, for example, in the publications GB 2 048 229 A, U.S. Pat. Nos. 4,775,528 A and 6,010,688 A. Activated aluminum salts typically have an HPLC-peak 4-to-peak 3 surface ratio of at least about 0.4, preferably of at least about 0.7, particularly of at least about 0.9, wherein at least 70% of the aluminum are associated with these HPLC-peaks.

In this context, "activated" aluminum zirconium salts are also known, which have a high HPLC-peak 5-aluminum content, particularly a peak 5 surface of at least about 33%, preferably of at least about 45%, relative to the total surface under peaks 2 to 5. measured with HPLC of 10 wt. % aqueous solution of the active ingredient under conditions in which the aluminum species are dissolved in at least 4 peaks in succession (identified as peaks 2 to 5). Preferred aluminum-zirconium salts with a high HPLC-peak 5-aluminum content (also designated as "$E^5AZCH$") are, for example, disclosed in the publications U.S. Pat. Nos. 6,436,381 A and 6,649,152 A. The aforementioned activated aluminum zirconium salt can also be stabilized with a water-soluble strontium salt and/or with a water-soluble calcium salt, as is disclosed in the publication U.S. Pat. No. 6,923,952 A, for example.

In the context of the present disclosure, basic calcium aluminum salts can be used as antiperspirant aluminum salts, as disclosed, for example, in the publication U.S. Pat. No. 2,571,030 A. These salts can be obtained by reacting calcium carbonate with aluminum chlorohydroxide or aluminum chloride and aluminum powder or by adding calcium chloride dihydrate to aluminum chlorohydroxide. It is also possible to use aluminum zirconium complexes, which are buffered with salts of amino acids, in particular with alkali and alkaline earth glycinates, and as disclosed, for example, in the publication U.S. Pat. No. 4,017,599 A.

As contemplated herein, particularly preferred antiperspirant aluminum salts have a molar metal-to-chloride ratio of from about 1.9 to about 2.1. The metal-to-chloride ratio of particularly preferred aluminum sesquichlorohydrates in the context of the present disclosure is from about 1.5:1 to about 1.8:1. Preferred aluminum zirconium tetrachlorohydrates have a molar ratio of Al:Zr of from about 2 to about 6 and of metal:chloride of from about 0.9 to about 1.3, wherein particular preference is given to salts with a molar metal-to-chloride ratio of from about 0.9 to about 1.1, preferably from about 0.9 to about 1.0.

The antiperspirant active ingredient, in particular at least one aforementioned aluminum salt and/or aluminum zirconium salt, is preferably used in specific quantity ranges. Preferred cosmetic agents as contemplated herein are therefore exemplified in that the at least one antiperspirant active ingredient is contained in a total quantity of from about 2.0 to about 40 wt. %, preferably from about 3.0 to about 35 wt. %, more preferably from about 4.0 to about 32 wt. %, even more preferably from about 5.0 to about 30 wt. %, particularly preferably from about 8.0 to about 25 wt. %, and most preferably from about 10 to about 20 wt. %, relative to the total weight of the cosmetic agent. The use of the aforementioned quantities of the at least one antiperspirant active ingredient ensures an adequate antiperspirant effect and does not result in skin intolerances or negative interactions with other ingredients of the agent as contemplated herein.

In addition to and/or instead of the aforementioned antiperspirant active ingredient, the cosmetic agent can contain at least one deodorizing active ingredient.

In the context of the present disclosure, it is preferred that the at least one deodorizing active ingredient is selected from the group of (i) silver salts; (ii) aromatic alcohols, in particular 2-benzylheptan-1-ol and mixtures of 2-benzylheptan-1-ol and phenoxyethanol; (iii) 1,2-alkanediols having from about 5 to about 12 carbon atoms, in particular 3-(2-ethylhexyloxy)-1,2-propanediol; (iv) triethyl citrates; (v) active ingredients against exoesterases, in particular against arylsulfatase, lipase, beta-glucuronidase and cystathionine β-lyase; (vi) cationic phospholipids; (vii) odor absorbers, in particular silicates, such as montmorillonite, kaolinite, illite, beidellite, nontronite, saponite, hectorite, bentonite, smectite and talcum, zeolites, zinc ricinoleate, cyclodextrins; (viii) deodorizing ion exchangers; (ix) germ-inhibiting agents; (x) prebiotically effective components; and (xi) mixtures thereof.

Preferably, the deodorizing active ingredient is used in specific quantity ranges. Preferred cosmetic agents as contemplated herein are therefore exemplified in that the at least one deodorizing active ingredient is contained in a total amount of from about 0.0001 to about 40 wt. %, preferably from about 0.2 to about 20 wt. %, more preferably from about 1.0 to about 15 wt. %, and particularly preferably from about 1.5 to about 5.0 wt. %, relative to the total weight of the cosmetic agent. The use of the aforementioned quantities of the at least one deodorizing active ingredient ensures an adequate deodorizing effect and does not result in negative interactions with other ingredients of the agent as contemplated herein.

Furthermore, thickening or crosslinking substances can be contained in order to adjust the viscosity of the cosmetic agent to the desired ranges for the respective application. As contemplated herein, the thickening or crosslinking substances used are preferably also designated as associative thickeners, preferably highly ethoxylated compounds with two or more long-chain alkyl substituents.

This preferably includes cross-linkers from the group of:
polyethylene glycol ethers of the general formula R—O—(—CH$_2$—CH$_2$—O—)$_n$—R', wherein R and R' independently denote branched or unbranched alkyl, aryl or alkenyl radicals and n is an integer greater than about 75, preferably an integer from about 100 to about 400, and particularly preferably an integer from about 120 to about 200, for example PEG-150 Distearate and/or PEG-150 Dioleate, etherified fatty acid ethoxylates of the general formula R—COO—(—CH$_2$—CH$_2$—O—)$_n$—R', wherein R and R' independently denote branched or unbranched alkyl, aryl or alkenyl radicals and n is an integer greater than about 75, preferably an integer from about 100 to about 400, and particularly preferably an integer from about 120 to about 200, esterified fatty acid ethoxylates of the general formula R—COO—(—CH$_2$—CH$_2$—O—)$_n$—C(O)—R', wherein R and R' independently denote branched or unbranched alkyl, aryl or alkenyl radicals and n is an integer greater than about 75, preferably an integer from about 100 to about 400, and particularly preferably an integer from about 120 to about 200, polypropylene glycol ethers of the general formula R—O—(—CH$_2$—CH(CH$_3$)—O—)$_n$—R', wherein R and R' independently denote branched or unbranched alkyl, aryl or alkenyl radicals and n is an integer greater than about 75, preferably an integer from about 100 to about 400, and particularly preferably an integer from about 120 to about 200, esterified fatty acid propoxylates of the general formula R—COO—(CH$_2$—CH(CH$_3$)—O—)$_n$—C(O)—R', wherein R and R' independently denote branched or unbranched alkyl, aryl or alkenyl radicals and n is an integer greater than about 75, preferably an integer from about 100 to about 400, and particularly preferably an integer from about 120 to about 200, polypropylene glycol ethers of the general formula R—O—X$_n$—Y$_m$—R' wherein R and R' denote branched or unbranched alkyl, aryl or alkenyl radicals, wherein X and Y are not identical and each denote either an oxyethylene group or an oxypropylene group, and n and m independently denote integers, the sum of which is greater than about 75, preferably an integer from about 100 to about 400, and particularly preferably an integer from about 120 to about 200 and etherified fatty acid propoxylates of the general formula R—COO—X$_n$—Y$_m$—R', wherein R and R' denote branched or unbranched alkyl, aryl or alkenyl radicals, wherein X and Y are not identical and each denote either an oxyethylene group or an oxypropylene group, and n and m independently denote integers, the sum of which is greater than about 75, preferably an integer from about 100 to about 400, and particularly preferably an integer from about 120 to about 200.

Among these, particular preference is given to polyalkylene glycol ethers of the general formula R—O—(CH$_2$—CH$_2$—O)$_n$—R' or R—O—(CH$_2$—CH(CH$_3$)—O)$_n$—R' and polyalkylene glycol esters of the general formula R—COO—(CH$_2$—CH$_2$—O)$_n$—C(O)—R' or R—COO—(CH$_2$—CH(CH$_3$)—O)$_n$—C(O)—R', wherein R and R' independently denote a linear or branched C$_6$-C$_{30}$ alkyl or C$_6$-C$_{30}$ alkenyl group, and n, the number of alkylenoxide units, denotes an integer greater than about 75, preferably an integer from about 100 to about 400, and particularly preferably an integer from about 120 to about 200. R and R' are preferably independently a decyl, undecyl, lauryl, tridecyl, tetradecyl, pentadecyl, hexadecyl, heptadecyl, heptadecenyl, octadecyl, octadecenyl, stearyl, oleyl, nonadecyl, nonadecenyl, eicosyl, eicosenyl, docosyl, docosenyl or behenyl group.

As contemplated herein, the polyethylene glycol ethers and polyethylene glycol esters are particularly preferable, in particular PEG-150 Distearate, PEG-150 Dioleate, PEG-120 Methyl Glucose Dioleate, PEG-300 Pentaerythrityl Tetraisostearate, PEG-350 Sorbitan Isostearate and PEG-230 Glyceryl Isostearate.

As a further, thickener, preferably at least one nonionic polyurethane polymer can be alternatively or additionally contained, comprising at least one polyurethane unit of the formula (Ib) and/or the formula (Ic), at least one nonionic polyether unit of the formula (IIa) and at least one ether unit of the formula (IIIb)

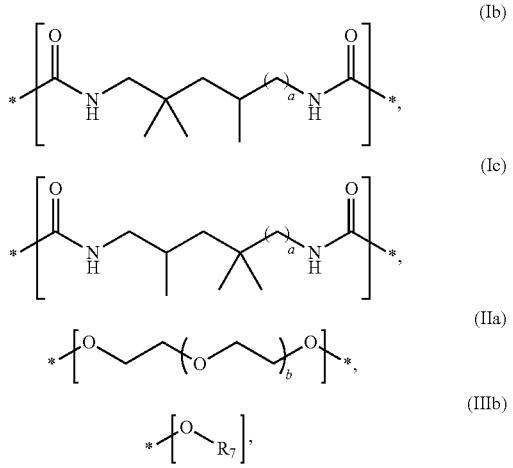

wherein
a denotes the integer 2,
b denotes integers from about 80 to about 110, and
$R_7$ denotes a branched $C_{16}$-$C_{20}$ alkyl group, The use of such nonionic polyurethane polymers in the cosmetic agents as contemplated herein permits a low total emulsifier concentration and can contribute to good storage stability under temperature fluctuations and good cosmetic properties. Due to the low total emulsifier concentration, these agents have excellent skin tolerances. In particular, the use of these polyurethane polymers leads to a thickening of preferred cosmetic agents, meaning that no further thickeners are contained in preferred embodiments of the present disclosure.

The use of non-ionic polyurethane polymers, which contain polyurethane units of the formulae (Ib) and/or (Ic), nonionic polyether units of the formula (IIa) and ether units of the formula (IIIb), and/or the aforementioned polyethylene glycol ethers of the general formula R—O—(—CH$_2$—CH$_2$—O—)$_n$—R', leads to a thickening of the emulsion, meaning that favorable viscosities can be achieved for roll-on-application. As contemplated herein, it is particularly preferred that the at least one nonionic polyurethane polymer is a copolymer of trimethylhexane diisocyanate (TMHDI) and polyethylene glycol with about 90 ethylene oxide units, terminally modified with a branched $C_{16}$-$C_{20}$ alcohol. For example, this is commercially available as Rheoluxe® 880 (Elementis), an approx. 30 wt. % solution/dispersion of to-$C_{16}$-$C_{20}$ isoalkoxy TMHDI/PEG-90 Copolymer in 1,2-propylene glycol (approx. 55 wt.-%) and water (approx. 15 wt.-%). Such nonionic polyurethane polymers have hydrophobic end groups in the form of branched $C_{16}$-$C_{20}$ alkyl groups and a hydrophilic middle part due to the use of polyethylene glycol. Consequently, such polyurethanes are also capable of effectively stabilizing and crosslinking micelles formed in the cosmetic agents.

The thickening agents or cross-linkers are preferably used in specific quantity ranges. As contemplated herein, it is preferred that the at least one thickener is contained in a total quantity of from about 0.2 to about 4.0 wt. %, preferably from about 0.5 to about 3.0 wt. %, more preferably from about 0.6 to about 2.0 wt. %, particularly preferably from about 0.7 to about 1.5 wt. %, and most preferably from about 0.8 to about 1.2 wt. %, relative to the total weight of the cosmetic agent. This leads to excellent stabilization of the preferred cosmetic agents as contemplated herein, without incompatibilities with other ingredients occurring. In particular, only the non-ionic polyurethane polymers described above, which contain at least one polyurethane unit of the formula (Ib) and/or (Ic), at least one non-ionic Polyether unit of the formula (IIa) and at least one ether unit of the formula (IIIb), and/or the aforementioned polyethylene glycol ethers of the general formula R—O—(—CH$_2$—CH$_2$—O—)$_n$—R', are preferably used as the thickener.

Other typical constituents of cosmetic agents, such as perfumes and preservatives, can be contained in the cosmetic agents of the present disclosure. As contemplated herein, perfumes are not considered oil components.

Particularly preferred cosmetic agents are exemplified in that they are provided in the form of an O/W emulsion, which is as transparent as possible, with a volume average particle diameter $D_{50}$ of from about 50 to about 1000 nm, preferably from about 100 to about 500 nm, particularly preferably from about 150 to about 400 nm, and most preferably from about 200 to about 300 nm. The volume average particle diameter of the particles or droplets present in the emulsion can be determined, for example, using laser diffraction (Roland I. et. al.; *Systematic characterization of oil-in-water emulsions for formulation design"; Int. J. of Pharmaceutics*, 2003, 263, pages 85 to 94). O/W emulsions having the aforementioned particle sizes are also designated as microemulsions in the context of the present disclosure. As contemplated herein, transparent O/W emulsions are understood as emulsions that have an NTU value (Nephelometric Turbidity Unit) of from about zero to about 150 NTU, preferably a maximum of about 80 NTU, particularly preferably a maximum of about 60 NTU, and most preferably a maximum of about 40 NTU, in each case measured at 22° C. The NTU value is a measurement of transparency and represents the turbidity of the emulsion measured with a calibrated nephelometer. The NTU value of the O/W emulsions as contemplated herein can be determined, for example, using a turbidimeter, as described in patent application WO2016012327 A2. At 22° C., cosmetic agents as contemplated herein have a measured turbidity according to DIN EN ISO 7027 (C2) 2016-11 of from about 0 to about 150 NTU, preferably up to about 80 NTU, more preferably up to about 60 NTU, particularly preferably up to about 40 NTU, and most preferably up to about 30 NTU.

The cosmetic agents as contemplated herein preferably have a transmission of about 92% or more, determined at 22° C. and with a light wavelength of 500 nm. As contemplated herein, a device such as LICO 400 (long), for example, can be used to determine the transmission.

The cosmetic agents as contemplated herein preferably have a viscosity in the range of from about 1200 to about 2500 cps (20° C., Brookfield DV-II+ Pro viscometer, Spindle 3, 20 rpm). As contemplated herein, the viscosity can preferably be adjusted in particular by one or more of the aforementioned thickeners.

O/W emulsions as contemplated herein can be produced using the methods known from the prior art.

The tables below show most preferred cosmetic agents as contemplated herein, which are provided in the form of an O/W emulsion with a volume average particle diameter $D_{50}$ of preferably from about 10 to about 400 nm, more preferably from about 10 to about 200 nm (all values in wt. %, unless otherwise stated):

| | K | K2 | K3 | K4 |
|---|---|---|---|---|
| Isopropylisostearate | 0.5 to 3.0 | 0.7 to 2.0 | 1.8 to 1.5 | 1.0 to 1.5 |
| Isopropyl myristate | 0.1 to 1.0 | 0.2 to 0.9 | 0.3 to 0.7 | 0.4 to 0.6 |
| Weight ratio of isopropylisostearate: Isopropyl myristate | 1.5:1 to 3.5:1 | 1.5:1 to 3.5:1 | 1.8:1 to 3.0:1 | 1.8:1 to 2.5:1 |
| Emulsifier: c1) ethoxylated, saturated, branched $C_{14}$-$C_{18}$ alcohol with an ethoxylation degree of 18 to 22 ethylene oxide units | 1.0 to 5.0 | 1.5 to 4.0 | 1.6 to 3.5 | 2.0 to 3.0 |
| Emulsifier c2) at least one ethoxylated, linear, mono-unsaturated $C_{16}$-$C_{20}$ alcohol with an ethoxylation degree of 18 to 22 ethylene oxide units | 0.5 to 3.5 | 0.7 to 3.0 | 0.8 to 1.5 | 0.8 to 1.3 |
| Emulsifier: Esters of isostearic acid with 1,2-propylene glycol | 0.1 to 1.7 | 0.2 to 1.5 | 0.3 to 1.2 | 0.4 to 1.0 |
| Emulsifier: hydrated castor oil with 20 to 60 EO | 0.1 to 4.0 | 0.2 to 3.0 | 0.3 to 2.0 | 0.5 to 1.5 |
| Antiperspirant active ingredient d) | 2.0 to 40 | 5.0 to 30 | 8.0 to 25 | 10 to 20 |
| Cosmetic carrier (aqueous or aqueous-glycolic carrier) | ad 100 | ad 100 | ad 100 | ad 100 |

| | K5 | K6 | K7 | K8 |
|---|---|---|---|---|
| Isopropylisostearate | 0.5 to 3.0 | 0.7 to 2.0 | 1.8 to 1.5 | 1.0 to 1.5 |
| Isopropyl myristate | 0.1 to 1.0 | 0.2 to 0.9 | 0.3 to 0.7 | 0.4 to 0.6 |
| Weight ratio of isopropylisostearate: Isopropyl myristate | 1.5:1 to 3.5:1 | 1.5:1 to 3.5:1 | 1.8:1 to 3.0:1 | 1.8:1 to 2.5:1 |
| Emulsifier: c1) ethoxylated, saturated, branched $C_{14}$-$C_{18}$ alcohol with an ethoxylation degree of 18 to 22 ethylene oxide units | 1.0 to 5.0 | 1.5 to 4.0 | 1.6 to 3.5 | 2.0 to 3.0 |
| Emulsifier c2) at least one ethoxylated, linear, mono-unsaturated $C_{16}$-$C_{20}$ alcohol with an ethoxylation degree of 18 to 22 ethylene oxide units | 0.5 to 3.5 | 0.7 to 3.0 | 0.8 to 1.5 | 0.8 to 1.3 |
| Emulsifier: Esters of isostearic acid with 1,2-propylene glycol | 0.1 to 1.7 | 0.2 to 1.5 | 0.3 to 1.2 | 0.4 to 1.0 |
| Emulsifier: hydrated castor oil with 20 to 60 EO | 0.1 to 4.0 | 0.2 to 3.0 | 0.3 to 2.0 | 0.5 to 1.5 |
| Deodorizing active ingredient d) | 0.0001 to 40 | 0.2 to 20 | 1.0 to 15 | 1.5 to 15 |
| Cosmetic carrier (aqueous or aqueous-glycolic carrier) | ad 100 | ad 100 | ad 100 | ad 100 |

| | K9 | K10 | K11 | K12 |
|---|---|---|---|---|
| Isopropylisostearate | 0.5 to 3.0 | 0.7 to 2.0 | 1.8 to 1.5 | 1.0 to 1.5 |
| Isopropyl myristate | 0.1 to 1.0 | 0.2 to 0.9 | 0.3 to 0.7 | 0.4 to 0.6 |
| Weight ratio of isopropylisostearate: Isopropyl myristate | 1.5:1 to 3.5:1 | 1.5:1 to 3.5:1 | 1.8:1 to 3.0:1 | 1.8:1 to 2.5:1 |
| Emulsifier c1) isoceteth-20 | 1.0 to 5.0 | 1.5 to 4.0 | 1.6 to 3.5 | 2.0 to 3.0 |
| Emulsifier c2) oleth-20 | 0.5 to 3.5 | 0.7 to 3.0 | 0.8 to 1.5 | 0.8 to 1.3 |
| Emulsifier: propylene glycol isostearate | 0.1 to 1.7 | 0.2 to 1.5 | 0.3 to 1.2 | 0.4 to 1.0 |
| Emulsifier: PEG-40 Hydrogenated Castor Oil | 0.1 to 4.0 | 0.2 to 3.0 | 0.3 to 2.0 | 0.5 to 1.5 |
| Antiperspirant active ingredient d): aluminum chlorohydrate and/or aluminum sesquichlorohydrate | 2.0 to 40 | 5.0 to 30 | 8.0 to 25 | 10 to 20 |
| Cosmetic carrier (aqueous or aqueous-glycolic carrier) | ad 100 | ad 100 | ad 100 | ad 100 |

-continued

|  | K13 | K14 | K15 | K16 |
|---|---|---|---|---|
| Isopropylisostearate | 0.5 to 3.0 | 0.7 to 2.0 | 1.8 to 1.5 | 1.0 to 1.5 |
| Isopropyl myristate | 0.1 to 1.0 | 0.2 to 0.9 | 0.3 to 0.7 | 0.4 to 0.6 |
| Weight ratio of isopropylisostearate: Isopropyl myristate | 1.5:1 to 3.5:1 | 1.5:1 to 3.5:1 | 1.8:1 to 3.0:1 | 1.8:1 to 2.5:1 |
| Emulsifier c1) isoceteth-20 | 1.0 to 5.0 | 1.5 to 4.0 | 1.6 to 3.5 | 2.0 to 3.0 |
| Emulsifier c2) oleth-20 | 0.5 to 3.5 | 0.7 to 3.0 | 0.8 to 1.5 | 0.8 to 1.3 |
| Emulsifier: propylene glycol isostearate | 0.1 to 1.7 | 0.2 to 1.5 | 0.3 to 1.2 | 0.4 to 1.0 |
| Emulsifier: PEG-40 Hydrogenated Castor Oil | 0.1 to 4.0 | 0.2 to 3.0 | 0.3 to 2.0 | 0.5 to 1.5 |
| Deodorizing active ingredient d) | 0.0001 to 40 | 0.2 to 20 | 1.0 to 15 | 1.5 to 15 |
| Cosmetic carrier (aqueous or aqueous-glycolic carrier) | ad 100 | ad 100 | ad 100 | ad 100 |

|  | K17 | K18 | K19 | K20 |
|---|---|---|---|---|
| Isopropylisostearate | 0.5 to 3.0 | 0.7 to 2.0 | 1.8 to 1.5 | 1.0 to 1.5 |
| Isopropyl myristate | 0.1 to 1.0 | 0.2 to 0.9 | 0.3 to 0.7 | 0.4 to 0.6 |
| Weight ratio of isopropylisostearate: Isopropyl myristate | 1.5:1 to 3.5:1 | 1.5:1 to 3.5:1 | 1.8:1 to 3.0:1 | 1.8:1 to 2.5:1 |
| Emulsifier: c1) ethoxylated, saturated, branched $C_{14}$-$C_{18}$ alcohol with an ethoxylation degree of 18 to 22 ethylene oxide units | 1.0 to 5.0 | 1.5 to 4.0 | 1.6 to 3.5 | 2.0 to 3.0 |
| Emulsifier c2) at least one ethoxylated, linear, mono-unsaturated $C_{16}$-$C_{20}$ alcohol with an ethoxylation degree of 18 to 22 ethylene oxide units | 0.5 to 3.5 | 0.7 to 3.0 | 0.8 to 1.5 | 0.8 to 1.3 |
| Emulsifier: Esters of isostearic acid with 1,2-propylene glycol | 0.1 to 1.7 | 0.2 to 1.5 | 0.3 to 1.2 | 0.4 to 1.0 |
| Emulsifier: hydrated castor oil with 20 to 60 EO | 0.1 to 4.0 | 0.2 to 3.0 | 0.3 to 2.0 | 0.5 to 1.5 |
| Antiperspirant active ingredient d) | 2.0 to 40 | 5.0 to 30 | 8.0 to 25 | 10 to 20 |
| Thickener* | 0.2 to 4.0 | 0.5 to 3.0 | 0.6 to 2.0 | 0.7 to 1.5 |
| Cosmetic carrier (aqueous or aqueous-glycolic carrier) | ad 100 | ad 100 | ad 100 | ad 100 |

|  | K21 | K22 | K23 | K24 |
|---|---|---|---|---|
| Isopropylisostearate | 0.5 to 3.0 | 0.7 to 2.0 | 1.8 to 1.5 | 1.0 to 1.5 |
| Isopropyl myristate | 0.1 to 1.0 | 0.2 to 0.9 | 0.3 to 0.7 | 0.4 to 0.6 |
| Weight ratio of isopropylisostearate: Isopropyl myristate | 1.5:1 to 3.5:1 | 1.5:1 to 3.5:1 | 1.8:1 to 3.0:1 | 1.8:1 to 2.5:1 |
| Emulsifier: c1) ethoxylated, saturated, branched $C_{14}$-$C_{18}$ alcohol with an ethoxylation degree of 18 to 22 ethylene oxide units | 1.0 to 5.0 | 1.5 to 4.0 | 1.6 to 3.5 | 2.0 to 3.0 |
| Emulsifier c2) at least one ethoxylated, linear, mono-unsaturated $C_{16}$-$C_{20}$ alcohol with an ethoxylation degree of 18 to 22 ethylene oxide units | 0.5 to 3.5 | 0.7 to 3.0 | 0.8 to 1.5 | 0.8 to 1.3 |
| Emulsifier: Esters of isostearic acid with 1,2-propylene glycol | 0.1 to 1.7 | 0.2 to 1.5 | 0.3 to 1.2 | 0.4 to 1.0 |
| Emulsifier: hydrated castor oil with 20 to 60 EO | 0.1 to 4.0 | 0.2 to 3.0 | 0.3 to 2.0 | 0.5 to 1.5 |
| Antiperspirant active ingredient d) | 2.0 to 40 | 5.0 to 30 | 8.0 to 25 | 10 to 20 |
| Thickener* | 0.2 to 4.0 | 0.5 to 3.0 | 0.6 to 2.0 | 0.7 to 1.5 |
| Cosmetic carrier (aqueous or aqueous-glycolic carrier) | ad 100 | ad 100 | ad 100 | ad 100 |

|  | K25 | K26 | K27 | K28 |
|---|---|---|---|---|
| Isopropylisostearate | 0.5 to 3.0 | 0.7 to 2.0 | 1.8 to 1.5 | 1.0 to 1.5 |
| Isopropyl myristate | 0.1 to 1.0 | 0.2 to 0.9 | 0.3 to 0.7 | 0.4 to 0.6 |
| Weight ratio of isopropylisostearate: Isopropyl myristate | 1.5:1 to 3.5:1 | 1.5:1 to 3.5:1 | 1.8:1 to 3.0:1 | 1.8:1 to 2.5:1 |

| | | | | |
|---|---|---|---|---|
| Emulsifier c1) isoceteth-20 | 1.0 to 5.0 | 1.5 to 4.0 | 1.6 to 3.5 | 2.0 to 3.0 |
| Emulsifier c2) oleth-20 | 0.5 to 3.5 | 0.7 to 3.0 | 0.8 to 1.5 | 0.8 to 1.3 |
| Emulsifier: propylene glycol isostearate | 0.1 to 1.7 | 0.2 to 1.5 | 0.3 to 1.2 | 0.4 to 1.0 |
| Emulsifier: PEG-40 Hydrogenated Castor Oil | 0.1 to 4.0 | 0.2 to 3.0 | 0.3 to 2.0 | 0.5 to 1.5 |
| Antiperspirant active ingredient d): aluminum chlorohydrate and/or aluminum sesquichlorohydrate | 2.0 to 40 | 5.0 to 30 | 8.0 to 25 | 10 to 20 |
| PEG-150-Distearate and/or PEG-150-Dioleate and/or a copolymer of trimethylhexane diisocyanate (TMHDI) and polyethylene glycol with 90 ethylene oxide units, terminally modified with a branched $C_{16}$-$C_{20}$ alcohol | 0.2 to 4.0 | 0.5 to 3.0 | 0.6 to 2.0 | 0.7 to 1.5 |
| Cosmetic carrier (aqueous or aqueous-glycolic carrier) | ad 100 | ad 100 | ad 100 | ad 100 |

| | K29 | K30 | K31 | K32 |
|---|---|---|---|---|
| Isopropylisostearate | 0.5 to 3.0 | 0.7 to 2.0 | 1.8 to 1.5 | 1.0 to 1.5 |
| Isopropyl myristate | 0.1 to 1.0 | 0.2 to 0.9 | 0.3 to 0.7 | 0.4 to 0.6 |
| Weight ratio of isopropylisostearate: Isopropyl myristate | 1.5:1 to 3.5:1 | 1.5:1 to 3.5:1 | 1.8:1 to 3.0:1 | 1.8:1 to 2.5:1 |
| Emulsifier c1) isoceteth-20 | 1.0 to 5.0 | 1.5 to 4.0 | 1.6 to 3.5 | 2.0 to 3.0 |
| Emulsifier c2) oleth-20 | 0.5 to 3.5 | 0.7 to 3.0 | 0.8 to 1.5 | 0.8 to 1.3 |
| Emulsifier: propylene glycol isostearate | 0.1 to 1.7 | 0.2 to 1.5 | 0.3 to 1.2 | 0.4 to 1.0 |
| Emulsifier: PEG-40 Hydrogenated Castor Oil | 0.1 to 4.0 | 0.2 to 3.0 | 0.3 to 2.0 | 0.5 to 1.5 |
| Deodorizing active ingredient d) | 0.0001 to 40 | 0.2 to 20 | 1.0 to 15 | 1.5 to 15 |
| PEG-150-Distearate and/or PEG-150-Dioleate and/or a copolymer of trimethylhexane diisocyanate (TMHDI) and polyethylene glycol with 90 ethylene oxide units, terminally modified with a branched $C_{16}$-$C_{20}$ alcohol | 0.2 to 4.0 | 0.5 to 3.0 | 0.6 to 2.0 | 0.7 to 1.5 |
| Cosmetic carrier (aqueous or aqueous-glycolic carrier) | ad 100 | ad 100 | ad 100 | ad 100 |

*Thickener: in particular polyethylene glycol ethers of the general formula R-O—(—$CH_2$—$CH_2$—O—)$_n$-R', wherein R and R' independently denote branched or unbranched alkyl, aryl or alkenyl radicals and n is an integer greater than about 75, preferably an integer from about 100 to about 400, and particularly preferably an integer from about 120 to about 200, preferably PEG-150 Distearate and/or PEG-150 Dioleate; and/or at least one non-ionic polyurethane polymer, which comprises at least one polyurethane unit of the formula (Ib) and/or the formula (Ic), at least one nonionic polyether unit of the formula (IIa) and at least one ether unit of the formula (IIIb),

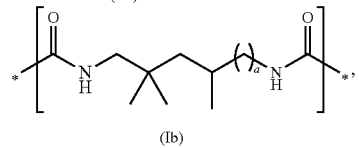

(Ib)

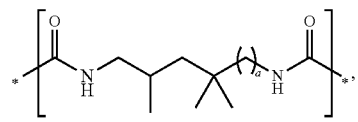

(Ic)

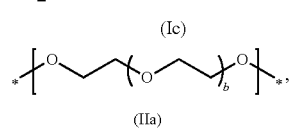

(IIa)

(IIIb)

wherein

*a* denotes the integer 2,

*b* denotes integers from about 80 to about 110, and $R_7$ denotes a branched $C_{16}$-$C_{20}$ alkyl group, preferably a copolymer of trimethylhexane diisocyanate (TMHDI) and polyethylene glycol with about 90 ethylene oxide units, terminally modified with a branched $C_{16}$-$C_{20}$-alcohol.

Another subject matter of the present disclosure is a non-therapeutic cosmetic method for reducing the perspiration of the body and/or for reducing the body odor released by perspiration, wherein a cosmetic agent as contemplated herein is applied to the human skin and remains on the application point for at least about 1 hour.

With respect to additional preferred embodiments of the methods as contemplated herein, particularly with regard to the cosmetic agents use there, the statements made about the cosmetic agents as contemplated herein apply mutatis mutandis.

The following examples explain the present disclosure without limiting it.

EXAMPLES

The quantities below are specified in wt. %, relative to the total weight of the cosmetic agents as contemplated herein.

The oil-soluble constituents were placed in a closed charging vessel, stirred and heated up to 70° C. The water and aluminum chlorohydrate were placed in a further closed charging vessel, stirred and heated up to 70° C. As soon as the aqueous solution reached a temperature of 70° C., it was slowly added to the oil phase. The mixture was then stirred and cooled to room temperature.

The results are shown in table 1 below.

TABLE 1

| Raw material | Example: 1 | 2 | 3 | 4 | 5 | 6 |
|---|---|---|---|---|---|---|
| Isoceteth-20 (Brij IC20N), Croda) | 2.8 | 2.0 | 2.8 | 2.8 | 2.0 | 2.8 |
| Oleth-20 (Brij O20, Croda) | 1.2 | 1.3 | 0.8 | 1.2 | 1.3 | 0.8 |
| Isopropyl isostearate (Crodamol IPIS, Croda) | 1.0 | 1.2 | 1.0 | 1.0 | 1.5 | 1.0 |
| Isopropyl myristate | 0.5 | 0.5 | 0.5 | 0.5 | 0.5 | 0.5 |
| PEG-40 Hydrated Castor Oil | 1.0 | 1.0 | 1.0 | 1.0 | 1.0 | 1.0 |
| Propylene glycol monoisostearate (Cithrol PGMIS, Croda) | 0.5 | 1.0 | 1.0 | 0.5 | 1.0 | 1.0 |
| 1,2-propanediol | 1.2 | 1.2 | 1.2 | 1.2 | 1.2 | 1.2 |
| Aluminum chlorohydrate (50% in water, Locron L, Clariant) | — | — | — | 26.8 | 26.3 | 26.3 |
| Aluminum sesquichlorohydrate (40% in water, Reach 301 L, SummitReheis) | 25.0 | 25.0 | 25.0 | — | — | — |
| Phenoxyethanol | 0.9 | 0.9 | 0.9 | 0.9 | 0.9 | 0.9 |
| Glycerol | 5.0 | 5.0 | 5.0 | 5.0 | 5.0 | 5.0 |
| Benzalkonium chloride (50% in water, Barquat DM-50) | 0.2 | 0.2 | 0.2 | 0.2 | 0.2 | 0.2 |
| PEG-150 Distearate (Eumulgin EO33. BASF) | 1.2 | 1.2 | — | 1.2 | 1.2 | 1.2 |
| Rheolirce 880 (Elementis) (INCI: Propylene glycol, to-$C_{16-20}$ isoalkoxy TMHDI/PEG-90 Copolymer, aqua (water)) | — | — | 3.0 | — | — | — |
| Perfume | 1.0 | 1.0 | 1.0 | 1.0 | 1.0 | 1.0 |
| Water | Ad 100 | Ad 100 | Ad 100 | Ad 100 | Ad 100 | Ad 100 |

Emulsions with a clear appearance were obtained at 22° C. The viscosity of the produced example compositions was in the range of 1200 to 2500 cps (20° C., Brookfield DV-II+Pro, Spindle 3, 20 rpm).

The cosmetic agents thus produced in the form of transparent O/W emulsions surprisingly have no sticky sensation after their application to the skin of test subjects. This could not be obtained with other oil components such as isopropylisostearate and isopropylmyristate in equal amounts, even if only one of the oil components was replaced, or the amount of one of the oil components was outside of the claimed range.

Furthermore, despite the low emulsifier content, a long shelf life and excellent skin tolerability was observed. Furthermore, the application of this agent leads to a high antiperspirant and/or deodorizing performance and a low residue formation on textiles. Furthermore, these agents have good usability and dosability.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

What is claimed is:

1. Cosmetic agent in the form of an O/W emulsion, comprising, in an aqueous cosmetically compatible carrier:
    a) Isopropylisostearate in a quantity of from about 0.5 to about 3.0 wt. %, based on the total weight of the cosmetic agent,
    b) Isopropylmyristate in a quantity of from about 0.1 to about 1.0 wt. %, based on the total weight of the cosmetic agent, wherein the weight ratio of the isopropylisostearate to the isopropylmyristate is from about 1.5:1 to about 3.5:1
    c) a non-ionic emulsifier, selected from c1) at least one ethoxylated, saturated, branched $C_{14}$-$C_{18}$ alcohol with an ethoxylation degree of from about 18 to about 22 ethylene oxide units, c2) at least one ethoxylated, linear, mono-unsaturated $C_{16}$-$C_{20}$ alcohol with an ethoxylation degree of from about 18 to about 22 of ethylene oxide units and c3) combinations thereof, d) at least one antiperspirant and/or deodorizing active ingredient,
at least one further non-ionic emulsifier, which is selected from hydrogenated castor oils with from about 20 mol to about 60 of ethylene oxide per mol of hydrogenated castor oil, esters of isostearic acid with 1,2-propylene glycol, and combinations thereof;
at least one polyethylene glycol ester of the general formula R—COO—(—CH$_2$—CH$_2$—O—)$_n$—C(O)—R', wherein R and R' independently denote branched or unbranched alkyl, aryl or alkenyl radicals and n is an integer greater than about 75; and/or at least one non-ionic polyurethane polymer, which comprises at least one polyurethane unit of the formula (Ib) and/or the formula (Ic), at least one nonionic polyether unit of the formula (IIa) and at least one ether unit of the formula (IIIb),

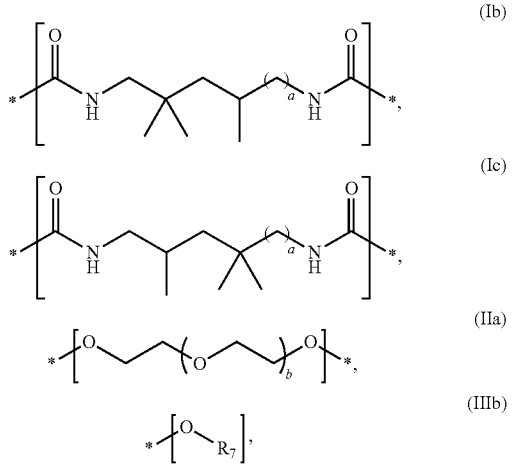

wherein
a denotes the integer 2,
b denotes integers from about 80 to 110, and
R$_7$ denotes a branched C$_{16}$-C$_{20}$ alkyl group
wherein the total quantity of emulsifier and oil components a) and b) in the cosmetic agent is from about 1.5 to about 8.0 wt. %, relative to the total weight of the cosmetic agent; and
from about 0.1 wt. % or less of ionic surfactants.

2. Cosmetic agent according to claim 1, wherein the total quantity of emulsifiers and oil components a) and b) in the cosmetic agent is from about 2.5 to about 6.0 wt. %, relative to the total weight of the cosmetic agent.

3. Cosmetic agent according to claim 1, wherein the isopropylisostearate is included in a quantity of from about 0.7 to about 1.5 wt. % and the isopropylmyristate is included in a quantity of from about 0.3 to about 0.7 wt. %, relative to the total weight of the cosmetic agent.

4. Cosmetic agent according to claim 1, wherein the weight ratio of isopropylisostearate to isopropylmyristate is from about 1.5:1 to about 3.5:1.

5. Cosmetic agent according to claim 1, wherein the non-ionic emulsifier c) is a combination c3) of non-ionic emulsifiers c1) and c2), wherein the weight ratio of non-ionic emulsifier c1) to non-ionic emulsifier c2) is from about 1.2:1 to about 3.5:1.

6. Cosmetic agent according to claim 1, wherein nonionic emulsifier c1) is polyoxyethylene (20) isocetyl ether (INCI: isoceteth-20) and nonionic emulsifier c2) is polyoxyethylene (20) oleyl ether (INCI: oleth-20).

7. Cosmetic agent according to claim 1, wherein the total quantity of non-ionic emulsifier c1) is from about 1.0 to about 5.0 wt. % and the total quantity of non-ionic emulsifier c2) is from about 0.5 to about 3.0 wt. %, relative to the total weight of the cosmetic agent.

8. Cosmetic agent according to claim 1, comprising at least one antiperspirant active ingredient in a total quantity of from about 2.0 to about 40 wt. %, relative to the total weight of the cosmetic agent.

9. Cosmetic agent according to claim 1, comprising at least one deodorizing active ingredient in a total quantity of from about 0.0001 to about 40 wt. %, relative to the total weight of the cosmetic agent.

10. Cosmetic agent according to claim 1, wherein the agent is provided in the form of an O1W emulsion with a volume average droplet size of from about 50 to about 1000 nm.

11. Cosmetic agent according to claim 1, wherein the agent has a viscosity of from about 1200 to about 2500 cps (20° C., Brookfield, Spindle 3, 20 rpm).

12. Cosmetic agent according to claim 1, wherein the agent has a measured turbidity according to DIN EN ISO 7027 (C2) 2016-11 at 22° C. of from about 0 to about 150 NTU.

13. Cosmetic agent according to claim 1, wherein the non-ionic emulsifier c) is a combination c3) of non-ionic emulsifiers c1) and c2), wherein the weight ratio of non-ionic emulsifier c1) to non-ionic emulsifier c2) is from about 1.5:1 to about 2.5:1.

14. Cosmetic agent according to claim 1, comprising at least one further non-ionic emulsifier, which is selected from hydrogenated castor oil with around about 40 mol of ethylene oxide per mol of hydrogenated castor oil (INCI: PEG-40 Hydrogenated Castor Oil), propylenglycolmonoisostearate, and combinations thereof.

15. Cosmetic agent according to claim 1, comprising at least one antiperspirant active ingredient in a total quantity of from about 10 to about 20 wt. %, relative to the total weight of the cosmetic agent.

16. Cosmetic agent according to claim 1, wherein R and R' independently denote branched or unbranched alkyl, aryl or alkenyl radicals and n is an integer from about 120 to about 200; and wherein the cosmetic agent further comprises the at least one non-ionic polyurethane polymer, which comprises at least one polyurethane unit of the formula (Ib) and/or the formula (Ic), at least one nonionic polyether unit of the formula (IIa) and at least one ether unit of the formula (IIIb).

17. Cosmetic agent according to claim 1 wherein the Isopropylisostearate is present in a quantity of about 0.5 wt. %, based on the total weight of the cosmetic agent.

18. Cosmetic agent according to claim 1 wherein the Isopropylisostearate is present in a quantity of about 3 wt. %, based on the total weight of the cosmetic agent.

19. Cosmetic agent according to claim 1 wherein the Isopropylmyristate is present in a quantity of about 0.1 wt. %, based on the total weight of the cosmetic agent.

20. Cosmetic agent according to claim 1 wherein the Isopropylmyristate is present in a quantity of about 1 wt. %, based on the total weight of the cosmetic agent.

* * * * *